(12) United States Patent
Cottard et al.

(10) Patent No.: US 7,651,537 B2
(45) Date of Patent: Jan. 26, 2010

(54) COMPOSITION FOR DYEING KERATIN FIBERS, COMPRISING 2,3-DIAMINO-6,7-DIHYDRO-1H,5H-PYRAZOLO[1,2-A]PYRAZOL-1-ONE, 6-CHLORO-2-METHYL-5-AMINOPHENOL AND A SUBSTITUTED META-AMINOPHENOL

(75) Inventors: François Cottard, Courbevoie (FR); Patricia Desenne, Bois Colombes (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/812,610

(22) Filed: Jun. 20, 2007

(65) Prior Publication Data

US 2008/0016628 A1   Jan. 24, 2008

Related U.S. Application Data

(60) Provisional application No. 60/818,272, filed on Jul. 5, 2006.

(30) Foreign Application Priority Data

Jun. 20, 2006  (FR) .................................. 06 52558

(51) Int. Cl.
  *A61Q 5/10*  (2006.01)
  *C07D 231/44*  (2006.01)
(52) U.S. Cl. ...................... 8/405; 8/406; 8/407; 8/408; 8/410; 8/411; 8/412; 8/421; 8/567; 548/369.1
(58) Field of Classification Search .................... 8/405, 8/406, 407, 408, 410, 411, 412, 421, 567; 514/406, 407; 548/369.1
See application file for complete search history.

(56) References Cited

U.S. PATENT DOCUMENTS

| | | | |
|---|---|---|---|
| 3,012,884 A | 12/1961 | de Ramaix et al. | |
| 4,003,699 A | 1/1977 | Rose et al. | |
| 4,128,425 A | 12/1978 | Greenwald | |
| RE30,199 E | 1/1980 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,718,731 A | 2/1998 | Loewe et al. | |
| 5,766,576 A | 6/1998 | Lowe et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,436,151 B2 | 8/2002 | Cottard et al. | |
| 6,645,258 B2 | 11/2003 | Vidal et al. | |
| 6,660,046 B1 | 12/2003 | Terranova et al. | |
| 6,730,789 B1 | 5/2004 | Birault et al. | |
| 7,285,137 B2 * | 10/2007 | Vidal et al. | 8/405 |
| 7,485,156 B2 | 2/2009 | Saunier | |
| 7,488,355 B2 | 2/2009 | Saunier | |
| 7,488,356 B2 | 2/2009 | Saunier | |
| 2001/0023514 A1 | 9/2001 | Cottard et al. | |
| 2002/0046431 A1 | 4/2002 | Laurent et al. | |
| 2002/0050013 A1 | 5/2002 | Vidal et al. | |
| 2002/0088062 A1 | 7/2002 | Pratt | |
| 2003/0019051 A9 | 1/2003 | Vidal et al. | |
| 2005/0166335 A1 | 8/2005 | Vidal et al. | |
| 2007/0006398 A1 | 1/2007 | Hercouet | |
| 2008/0005853 A1 | 1/2008 | Cottard et al. | |
| 2008/0016627 A1 | 1/2008 | Cottard et al. | |
| 2008/0016628 A1 | 1/2008 | Cottard et al. | |
| 2009/0007347 A1 | 1/2009 | Cottard et al. | |

FOREIGN PATENT DOCUMENTS

| | | |
|---|---|---|
| CH | 421 343 | 9/1966 |
| DE | 1 959 009 | 12/1970 |
| DE | 23 59 399 A1 | 6/1975 |
| DE | 38 43 892 A1 | 6/1990 |

(Continued)

OTHER PUBLICATIONS

STIC Search Report dated Jul. 31, 2008.*
French Search Report for FR 0652558, dated Mar. 9, 2007.
English language abstract of EP 0 770 375 B1, May 2, 1997.
English language abstract of JP 2-19576, Jan. 23, 1990.
English language abstract of JP 5-163124, Jun. 29, 1993.
English language abstract of DE 101 48 847 A1, May 10, 2003.
English language esp@cenet abstract of FR 2 801 308, May 25, 2001.
EP Search Report for EP 07 12 1666, dated Apr. 2, 2008.
French Search Report for FR 0652557, dated Mar. 9 2007.
French Search Report for FR 0652549, dated Mar. 6 2007.
French Search Report for FR 0655213, dated Nov. 30, 2006.
French Search Report for FR 0655214, dated Jul. 25, 2007.

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to a composition for dyeing keratin fibers, comprising 2,3-diamino-6,7-dihydro-1H,5H-pyrazolo[1,2-a]pyrazol-1-one as first oxidation base, 6-chloro-2-methyl-5-aminophenyl as first coupler and a substituted meta-aminophenol of given formula as second coupler, it being understood that the at least one first oxidation base and the at least one first coupler are present in a mole ratio of less than 1.5, the at least one first oxidation base and the at least one second coupler are present in a mole ratio of greater than 1, and the molar amount of the at least one first oxidation base is greater than or equal to $2.5 \times 10^{-3}$ mol per 100 g of composition. One aspect of the present disclosure makes it possible to obtain a strong, very chromatic, aesthetic, sparingly selective and/or fast coloration of keratin fibers in coppery shades. Further, the present disclosure makes it possible to obtain a strong coloration at a neutral pH.

16 Claims, No Drawings

FOREIGN PATENT DOCUMENTS

| | | |
|---|---|---|
| DE | 41 33 957 A1 | 4/1993 |
| DE | 195 43 988 A1 | 5/1997 |
| DE | 196 19 112 | 11/1997 |
| DE | 101 48 847 A1 | 5/2003 |
| EP | 0 770 375 B1 | 5/1997 |
| EP | 0 873 745 | 10/1998 |
| EP | 1 250 909 | 10/2002 |
| EP | 1550 656 A1 * | 6/2005 |
| EP | 1 550 656 A1 | 7/2005 |
| FR | 2 586 913 A1 | 3/1987 |
| FR | 2 733 749 A1 | 11/1996 |
| FR | 2 750 048 A1 | 12/1997 |
| FR | 2 801 308 A1 | 5/2001 |
| FR | 2 886 132 | 12/2006 |
| FR | 2 886 135 | 12/2006 |
| FR | 2 886 136 | 12/2006 |
| FR | 2 886 137 | 12/2006 |
| FR | 2 886 138 | 12/2006 |
| FR | 2 886 139 | 12/2006 |
| FR | 2 886 140 | 12/2006 |
| FR | 2 886 141 | 12/2006 |
| FR | 2 886 142 | 12/2006 |
| FR | 2 902 323 | 12/2007 |
| FR | 2 902 327 | 12/2007 |
| FR | 2 902 328 | 12/2007 |
| GB | 1 005 233 | 9/1965 |
| GB | 1 026 978 | 4/1966 |
| GB | 1 153 196 | 5/1969 |
| GB | 1 486 576 | 11/1974 |
| JP | 2-19576 | 1/1990 |
| JP | 5-163124 | 6/1993 |
| JP | 2002-535312 | 10/2002 |
| WO | WO 94/08969 | 4/1994 |
| WO | WO 94/08970 | 4/1994 |
| WO | WO 96/15765 | 5/1996 |

OTHER PUBLICATIONS

Office Action dated Oct. 27, 2008, in co-pending U.S. Appl. No. 11/987,450.
Office Action dated Aug. 4, 2008, in co-pending U.S. Appl. No. 11/812,603.
Office Action dated Oct. 28, 2008, in co-pending U.S. Appl. No. 11/987,451.
Office Action dated Aug. 15, 2008, in co-pending U.S. Appl. No. 11/812,616.
Co-pending U.S. Appl. No. 10/999,999, filed Dec. 1, 2004.
Co-pending U.S. Appl. No. 11/812,603, filed Jun. 20, 2007.
Co-pending U.S. Appl. No. 11/812,616, filed Jun. 20, 2007.
Co-pending U.S. Appl. No. 11/898,438, filed Sep. 12, 2007.
Co-pending U.S. Appl. No. 11/987,450, filed Nov. 30, 2007.
Co-pending U.S. Appl. No. 11/987,451, filed Nov. 30, 2007.
English language Abstract of DE 1 959 009, dated Dec. 3, 1970.
English language Abstract of DE 196 19 112, dated Nov. 13, 1997.
English language Abstract of EP 0 873 745, dated Oct. 28, 1998.
English language Abstract of EP 1 250 909, dated Oct. 23, 2002.
English language Abstract of FR 2 886 135, dated Dec. 1, 2006.
English language Abstract of FR 2 886 136, dated Dec. 1, 2006.
English language Abstract of FR 2 886 140, dated Dec. 1, 2006.
English language Abstract of FR 2 886 141, dated Dec. 1, 2006.
English language Abstract of FR 2 886 142, dated Dec. 1, 2006.
Helvetica Chimica Acta., vol. XXXIII, Fasciculus V (1950), No. 152, pp. 1183-1194.
Morissette et al., Advanced Drug Delivery Reviews, 2004, 56, pp. 275-300.
Notice of Allowance mailed Jun. 26, 2007, in co-pending U.S. Appl. No. 10/999,999.
Notice of Allowance mailed Mar. 9, 2007, in co-pending U.S. Appl. No. 10/999,999.
Notice of rejection in Japanese Application No. 2004-348020, mailed Dec. 6, 2005.
Notice of rejection in Japanese Application No. 2004-348020, mailed Jan. 29, 2008.
Office Action mailed Apr. 14, 2009, in co-pending U.S. Appl. No. 11/812,616.
Office Action mailed Apr. 27, 2009, in co-pending U.S. Appl. No. 11/987,451.
Office Action mailed Mar. 2, 2009, in co-pending U.S. Appl. No. 11/898,438.
Office Action mailed Mar. 24, 2009, in co-pending U.S. Appl. No. 11/812,603.
Office Action mailed May 1, 2009, in co-pending U.S. Appl. No. 11/987,450.
STIC Search Report for U.S. Appl. No. 10/999,999, dated Dec. 13, 2006.
STIC Search Report for U.S. Appl. No. 11/812,603, dated Jul. 13, 2008.
Vippagunta, S.R., "Crystalline Solids," Advanced Drug Delivery Reviews, 2001, 48, pp. 3-26.

* cited by examiner

COMPOSITION FOR DYEING KERATIN FIBERS, COMPRISING 2,3-DIAMINO-6,7-DIHYDRO-1H,5H-PYRAZOLO[1,2-A]PYRAZOL-1-ONE, 6-CHLORO-2-METHYL-5-AMINOPHENOL AND A SUBSTITUTED META-AMINOPHENOL

This application claims benefit of U.S. Provisional Application No. 60/818,272, filed Jul. 5, 2006, the contents of which are incorporated herein by reference. This application also claims benefit of priority under 35 U.S.C. § 119 to French Patent Application No. FR 0652558, filed Jun. 20, 2006, the contents of which are also incorporated herein by reference.

The present disclosure relates to a composition for dyeing keratin fibers, for instance human keratin fibers such as the hair, comprising 2,3-diamino-6,7-dihydro-1H,5H-pyrazolo[1,2-a]pyrazol-1-one as a first oxidation base, 6-chloro-2-methyl-5-aminophenol as a first coupler and a substituted meta-aminophenol as a second coupler.

It is known practice to dye keratin fibers, for instance human keratin fibers such as the hair, with dye compositions comprising oxidation dye precursors, for example ortho- or para-phenylenediamines, ortho- or para-aminophenols, and heterocyclic compounds such as diaminopyrazole derivatives, pyrazolo[1,5-a]pyrimidine derivatives, pyrimidine derivatives, pyridine derivatives, indole derivatives and indoline derivatives, which are generally known as oxidation bases. Oxidation dye precursors, or oxidation bases, are generally colorless or weakly colored compounds that, when combined with oxidizing products, can give rise to dyes or colored compounds via a process of oxidative condensation. Permanent colorations are thus obtained.

It is also known that the shades obtained with these oxidation bases may be varied by combining them with couplers or coloration modifiers, the latter being chosen for instance from meta-phenylenediamines, meta-aminophenols, meta-hydroxyphenols and certain heterocyclic compounds.

The variety of molecules used with respect to the oxidation bases and couplers allows a wide range of colors to be obtained.

The use of oxidation bases such as para-phenylenediamine and para-aminophenol derivatives allows a quite broad range of colors to be obtained at basic pH without, however, achieving shades with good chromaticity, while at the same time giving the hair excellent properties in terms of strength of color, uniformity of the color and fastness with respect to external agents.

However, the use of these bases at neutral pH generally does not allow a varied range of shades to be produced, for example, for warm shades such as reds and oranges.

Thus, it would be desirable to provide novel compositions for dyeing keratin fibers that make it possible to obtain a strong, chromatic, aesthetic and/or sparingly selective coloration in coppery shades, which shows good resistance to one or more of the various attacking factors to which the hair may be subjected, such as shampoo, light, sweat and permanent reshaping operations.

Accordingly, one aspect of the present disclosure is a composition for dyeing keratin fibers, comprising, in a medium suitable for dyeing:
at least one first oxidation base chosen from 2,3-diamino-6,7-dihydro-1H,5H-pyrazolo[1,2-a]pyrazol-1-one of formula (I) below, and the addition salts thereof:

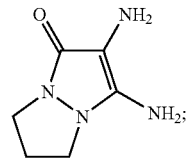

(I)

at least one first coupler chosen from 6-chloro-2-methyl-5-aminophenol, and the addition salts thereof; and
at least one second coupler chosen from the substituted meta-aminophenols of formula (II) below, and the addition salts thereof:

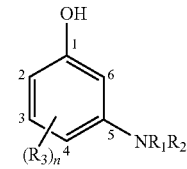

(II)

wherein:
$R_1$ and $R_2$, which may be identical or different, are each chosen from a hydrogen atom; an alkyl radical; a monohydroxyalkyl radical; a polyhydroxyalkyl radical; and a monoaminoalkyl radical; or
$R_1$ and $R_2$ form, together with the nitrogen atom to which they are attached, a saturated or unsaturated, 5- to 7-membered cyclic group comprising at least one heteroatom, which may be unsubstituted or substituted with at least one radical chosen from carboxyl, carboxamido, hydroxyl, amino, monoalkylamino and dialkylamino radicals, and alkyl radicals optionally substituted with at least one radical chosen from hydroxyl, amino, monoalkylamino and dialkylamino radicals;
$R_3$, independently, is chosen from a halogen atom; an alkyl radical; an alkoxy radical; a monohydroxyalkyl radical; a polyhydroxyalkyl radical; a monohydroxyalkoxy radical; and a polyhydroxyalkoxy radical;
n is an integer ranging from 0 to 4;
with the provisos that:
when n is equal to 0, then at least one of the radicals $R_1$ and $R_2$ is other than a hydrogen atom;
when n is equal to 2 and $R_3$ represents a methyl radical and a chlorine atom, respectively, in positions 2 and 6, then $R_1$ and $R_2$ do not simultaneously represent a hydrogen atom;
it being understood that the at least one first oxidation base and the at least one first coupler are present in a mole ratio of less than 1.5, the at least one first oxidation base and the at least one second coupler are present in a mole ratio greater than 1, and the molar amount of the at least one first oxidation base is greater than or equal to $2.5 \times 10^{-3}$ mol per 100 g of composition.

The dyeing composition of the present disclosure allows keratin fibers to be colored in coppery shades, for instance a coloration on natural or permanent-waved grey hair containing 90% white hairs having, according to the CIELab notation, a value for L* of less than or equal to 50, a value for a* of greater than or equal to 20, for example greater than or equal to 25, and even further, for instance from 25 to 50, a value for b* of greater than or equal to 20, for instance greater than or equal to 25, and even further for example, ranging from 25 to 50, and a ratio b*/a* ranging from 0.5 to 1.5, for example, from 0.7 to 1.2.

The dyeing composition of the present disclosure also makes it possible to obtain a strong, very chromatic, aesthetic, and/or sparingly selective coloration that shows good resistance to one or more of the various attacking factors to which the hair may be subjected, such as shampoo, light, sweat and permanent reshaping operations. Further, the present disclosure makes it possible to obtain an intense coloration at a neutral pH.

Another aspect of the present disclosure is a process for dyeing keratin fibers using the composition of the present disclosure, and also the use of this composition for dyeing keratin fibers.

Another aspect of the present disclosure is a dyeing kit comprising at least one first compartment comprising at least one dye composition comprising 2,3-diamino-6,7-dihydro-1H,5H-pyrazolo[1,2-a]pyrazol-1-one as oxidation base, 6-chloro-2-methyl-5-aminophenol as first coupler and a substituted meta-aminophenol as second coupler, and, at least one second compartment comprising at least one composition that comprises at least one oxidizing agent.

The CIELab notation used in the context of the present disclosure defines a calorimetric space in which each color is defined by three parameters (L*, a*, b*). The parameter L* reflects the lightness of the color, the value L* being equal to 0 for black and equal to 100 for absolute white. The higher the value of L*, the less intense the coloration. The parameter a* corresponds to the axis of the green/red antagonist pair. The parameter b* corresponds to the axis of the blue/yellow antagonist pair.

Unless otherwise indicated, the limits of the ranges of values given in the context of the present disclosure are included in these ranges.

In the context of the present disclosure, the term "alkyl radical" means, unless otherwise indicated, linear or branched $C_1$-$C_{10}$, for instance $C_1$-$C_6$, and even further, for example, $C_1$-$C_4$, alkyl radicals, such as methyl, ethyl, propyl, isopropyl, isobutyl, tert-butyl, pentyl or hexyl radicals.

In the context of the present disclosure, the at least one heteroatom may be chosen from an oxygen atom, a nitrogen atom, a sulfur atom and a phosphorus atom.

In the context of the present disclosure, a halogen atom may be chosen from a chlorine atom, a bromine atom, an iodine atom and a fluorine atom.

According to at least one embodiment of the present disclosure, $R_1$ and $R_2$, independently of each other, are each chosen from a hydrogen atom; an alkyl radical such as a methyl or ethyl radical; a monohydroxyalkyl radical such as a β-hydroxyethyl or γ-hydroxypropyl radical; or $R_1$ and $R_2$ form, together with the nitrogen atom to which they are attached, a ring chosen from pyrrolidine, piperidine, homopiperidine, piperazine, homopiperazine and morpholine heterocycles; where the said ring(s) are optionally substituted with at least one radical chosen from hydroxyl, amino, mono ($C_1$-$C_2$)alkylamino, di($C_1$-$C_2$)alkylamino, carboxyl and carboxamido radicals, or from $C_1$-$C_4$ alkyl radicals optionally substituted with at least one radical chosen from hydroxyl, amino, mono($C_1$-$C_2$)alkylamino and di($C_1$-$C_2$)alkylamino radicals. According to at least one further embodiment, the ring(s) formed are chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(β-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, N-(2-hydroxy-ethyl)homopiperazine, piperazine, 4-methylpiperazine, 4-ethylpiperazine, 4-(β-hydroxyethyl)piperazine and morpholine. For example, $R_1$ and $R_2$ may form, together with the nitrogen atom to which they are attached, one of the following groups: pyrrolidin-1-yl; piperidin-1-yl; piperazin-1-yl; 4-methylpiperazin-1-yl; 4-ethylpiperazin-1-yl; or 4-(β-hydroxyethyl)piperazin-1-yl; morpholin-4-yl.

According to at least one embodiment of the present disclosure, $R_3$ is chosen from a halogen atom, an alkyl radical, an alkoxy radical, and a monohydroxyalkoxy radical. In a further embodiment, $R_3$ is chosen from a chlorine atom, a methyl radical, a methoxy radical and a β-hydroxyethyloxy radical.

According to at least one embodiment of the present disclosure, n ranges from 0 to 2. In one embodiment, n is equal to 1 or 2. For instance, according to at least one embodiment, when n is equal to 1, $R_3$ may be in position 2 and when n is equal to 2, $R_3$ may be in positions 2 and 4.

Among the substituted meta-aminophenols of formula (II) that are useful in the context of the present disclosure, non-limiting mention may be made, for instance, of 5-amino-2-methoxyphenol; 5-amino-2-(β-hydroxyethyloxy)phenol; 5-amino-2-methylphenol; 5-N-(β-hydroxyethyl)amino-2-methylphenol; 5-N-(β-hydroxyethyl)amino-4-methoxy-2-methyl phenol; 5-amino-4-methoxy-2-methylphenol; 5-amino-4-chloro-2-methylphenol; 5-amino-2,4-dimethoxyphenol; 5-(γ-hydroxypropylamino)-2-methylphenol; 3-dimethylaminophenol; 2-methyl-5-dimethylaminophenol; 2-ethyl-5-dimethylaminophenol; 2-methoxy-5-dimethylaminophenol; 2-ethoxy-5-dimethylaminophenol; 2-(β-hydroxyethyl)-5-dimethylaminophenol; 3-diethylaminophenol; 2-methyl-5-diethylaminophenol; 2-ethyl-5-diethylaminophenol; 2-methoxy-5-diethylaminophenol; 2-ethoxy-5-diethylaminophenol; 2-(β-hydroxyethyl)-5-diethylaminophenol; 3-di(β-hydroxyethyl)aminophenol; 2-methyl-5-di(β-hydroxyethyl)aminophenol; 2-ethyl-5-di(β-hydroxyethyl)aminophenol; 2-methoxy-5-di(β-hydroxyethyl)aminophenol; 2-ethoxy-5-di(β-hydroxyethyl)aminophenol; 2-(β-hydroxyethyl)-5-di(β-hydroxyethyl)aminophenol; 3-pyrrolidin-1-ylphenol; 2-methyl-5-pyrrolidin-1-ylphenol; 2-ethyl-5-pyrrolidin-1-yl phenol; 2-methoxy-5-pyrrolidin-1-ylphenol; 2-ethoxy-5-pyrrolidin-1-ylphenol; 2-(β-hydroxyethyl)-5-pyrrolidin-1-ylphenol; 3-piperidin-1-ylphenol; 2-methyl-5-piperidin-1-ylphenol; 2-ethyl-5-piperidin-1-ylphenol; 2-methoxy-5-piperidin-1-ylphenol; 2-ethoxy-5-piperidin-1-ylphenol; 2-(β-hydroxyethyl)-5-piperidin-1-ylphenol; 3-piperazin-1-ylphenol; 2-methyl-5-piperazin-1-ylphenol; 2-ethyl-5-piperazin-1-ylphenol; 2-methoxy-5-piperazin-1-ylphenol; 2-ethoxy-5-piperazin-1-ylphenol; 2-(β-hydroxyethyl)-5-piperazin-1-ylphenol; 3-(4-methylpiperazin-1-yl)phenol; 2-methyl-5-(4-methylpiperazin-1-yl)phenol; 2-ethyl-5-(4-methylpiperazin-1-yl)phenol; 2-methoxy-5-(4-methylpiperazin-1-yl)phenol; 2-ethoxy-5-(4-methylpiperazin-1-yl)phenol; 2-(β-hydroxyethyl)-5-(4-methylpiperazin-1-yl)phenol; 3-(4-ethylpiperazin-1-yl)phenol; 2-methyl-5-(4-ethylpiperazin-1-yl)phenol; 2-ethyl-5-(4-ethylpiperazin-1-yl)phenol; 2-methoxy-5-(4-ethylpiperazin-1-yl)phenol; 2-ethoxy-5-(4-ethylpiperazin-1-yl)phenol; 2-(β-hydroxyethyl)-5-(4-ethylpiperazin-1-yl)phenol; 3-(4-(β-hydroxyethyl) piperazin-1-yl)phenol; 2-methyl-5-(4-(β-hydroxyethyl) piperazin-1-yl)phenol; 2-ethyl-5-(4-(β-hydroxyethyl) piperazin-1-yl)phenol; 2-methoxy-5-(4-(β-hydroxyethyl) piperazin-1-yl)phenol; 2-ethoxy-5-(4-(β-hydroxyethyl) piperazin-1-yl)phenol; 2-(β-hydroxyethyl)-5-(4-(β-hydroxyethyl)piperazin-1-yl)phenol; 3-morpholin-4-ylphenol; 2-methyl-5-morpholin-4-ylphenol; 2-ethyl-5-morpholin-4-ylphenol; 2-methoxy-5-morpholin-4-ylphenol; 2-ethoxy-5-morpholin-4-ylphenol; and 2-(β-hydroxyethyl)-5-morpholin-4-ylphenol.

According to at least one embodiment, the substituted meta-aminophenols of formula (II) mentioned above, may be chosen from 5-N-(β-hydroxyethylamino)-2-methyl-phenol and 5-amino-2-methylphenol.

In the composition in accordance with the present disclosure, the at least one first oxidation base/at least one first coupler mole ratio is less than 1.5. According to at least one embodiment, the at least one first oxidation base/at least one first coupler mole ratio ranges from 0.5 to 1.2.

According to at least one embodiment of the present disclosure, the at least one first oxidation base/at least one second coupler mole ratio is greater than 1. For instance, the at least one first oxidation base/at least one second coupler mole ratio ranges from 2 to 5.

The dye composition of the present disclosure may comprise at least one second oxidation base chosen from para-aminophenols.

Among the para-aminophenols that may be used as oxidation bases in the dye compositions in accordance with the present disclosure, non-limiting mention may be made of the compounds corresponding to formula (III) below, and the addition salts thereof:

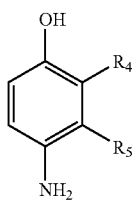

(III)

wherein:
R₄ is chosen from a hydrogen atom, a halogen atom, an alkyl radical, a monohydroxyalkyl radical, an alkoxyalkyl radical, an aminoalkyl radical, and a hydroxyalkylaminoalkyl radical;
R₅ is chosen from a hydrogen atom, a halogen atom, an alkyl radical, a monohydroxyalkyl radical, a polyhydroxyalkyl radical, an aminoalkyl radical, a cyanoalkyl radical, and an alkoxyalkyl radical;
where it is understood that at least one of the radicals R₄ or R₅ is a hydrogen atom.

Among the para-aminophenols of formula (III) above, non-limiting mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol. For instance, according to at least one embodiment of the present disclosure, para-aminophenol is used.

The dye composition of the present disclosure may comprise oxidation bases, other than those already disclosed, conventionally used for the dyeing of keratin fibers.

The composition of the present disclosure may comprise, for example, at least one oxidation base chosen from para-phenylenediamines, bis(phenyl)alkylenediamines, bis-para-aminophenols, ortho-aminophenols, ortho-phenylenediamines and heterocyclic bases other than 2,3-diamino-6,7-dihydro-1H,5H-pyrazolo[1,2-a]pyrazol-1-one, and the addition salts thereof.

The para-phenylenediamines that may be mentioned, for example, include but are not limited to para-phenylenediamine, para-toluenediamine, 2-chloro-para-phenylenediamine, 2,3-dimethyl-para-phenylenediamine, 2,6-dimethyl-para-phenyl-enediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof.

Among the para-phenylenediamines mentioned above, in at least one embodiment, 2-isopropyl-para-phenylenediamine, 2-β-hydroxyethyl-para-phenylene-diamine, 2-β-hydroxyethyloxy-para-phenylenediamine, 2,6-dimethyl-para-phenylenediamine, 2,6-diethyl-para-phenylenediamine, 2,3-dimethyl-para-phenyl-enediamine, N,N-bis(β-hydroxyethyl)-para-phenylenediamine, 2-chloro-para-phenylenediamine and 2-β-acetylaminoethyloxy-para-phenylenediamine, and the addition salts thereof may be used.

Among the bis(phenyl)alkylenediamines, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl) tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

The ortho-aminophenols that may be mentioned, for example, include but are not limited to 2-aminophenol, 2-amino-5-methylphenol, 2-amino-6-methylphenol and 5-acetamido-2-aminophenol, and the addition salts thereof.

Among the heterocyclic bases, non-limiting mention may be made, for example, of pyridine derivatives, pyrimidine derivatives and pyrazole derivatives.

The pyridine derivatives that may be mentioned include but are not limited to the compounds described, for example, in patents GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl) amino-3-amino-6-methoxypyridine and 3,4-diaminopyridine, and the addition salts thereof.

Other pyridine oxidation bases that are useful in the present disclosure are the 3-aminopyrazolo[1,5-a]pyridine oxidation bases or the addition salts thereof described, for example, in patent application FR 2 801 308. By way of example, non-limiting mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-yl-pyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxy-ethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol, and also the addition salts thereof.

The pyrimidine derivatives that may be mentioned include but are not limited to the compounds described, for example, in patents DE 2 359 399; JP 88-169 571; JP 05-63 124; EP 0 770 375 or patent application WO 96/15765, such as 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; and 3-amino-5-methyl-7-imidazolylpropylaminopyrazolo[1,5-a]pyrimidine, and the addition salts thereof and the tautomeric forms thereof, when a tautomeric equilibrium exists.

The pyrazole derivatives that may be mentioned, for example, include but are not limited to the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

The at least one dye composition of the present disclosure may comprise additional couplers, other than those already disclosed, conventionally used for dyeing keratin fibers.

For instance, the dye composition of the present disclosure may comprise, for example, at least one additional coupler chosen from meta-phenylenediamines, meta-aminophenols other than 6-chloro-2-methyl-5-aminophenol, the meta-aminophenols of formula (II); and the addition salts thereof, meta-diphenols, naphthalene-based couplers and heterocyclic couplers.

Further examples that may be mentioned include, but are not limited to, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

For instance, according to at least one embodiment, the presently disclosed dye composition comprises at least one additional coupler chosen from 2-amino-3-hydroxypyridine and 1,3-dihydroxy-2-methylbenzene, and the addition salts thereof.

The oxidation base(s) present in the dye composition of the present disclosure is (are) generally present in an amount ranging from 0.001% to 10% by weight for each, and further for example, 0.005% to 6% by weight for each, relative to the total weight of the dye composition.

The couplers present in the dye composition of the present disclosure are generally present in an amount ranging from 0.001% and 10% by weight for each, and according to at least one embodiment are present in an amount ranging from 0.005% to 6% by weight for each, relative to the total weight of the dye composition.

In general, the addition salts of the oxidation bases and of the couplers that may be used in the context of the present disclosure are chosen, for instance, from the addition salts with an acid, such as the hydrochlorides, hydrobromides, sulfates, citrates, succinates, tartrates, lactates, ($C_1$-$C_4$)alkylsulfonates, tosylates, benzenesulfonates, phosphates and acetates, and the addition salts with a base, such as sodium hydroxide, potassium hydroxide, ammonia, amines or alkanolamines.

The medium that is suitable for dyeing, also known as the dye support, is a cosmetic medium that generally comprises water and/or a mixture of water and at least one organic solvent to dissolve the compounds which would not be sufficiently soluble in water. As organic solvents, non-limiting mention may be made, for example, of $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The solvents may be present in an amount ranging from 1% to 40% by weight, relative to the total weight of the dye composition, and even further, for example from 5% to 30% by weight.

The dye composition in accordance with the present disclosure can also comprise various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, including, for example, anionic, cationic, nonionic or amphoteric associative polymeric thickeners, antioxidants, penetrants, sequestrants, fragrances, buffers, dispersants, conditioning agents, for instance silicones, which may be volatile or non-volatile, and modified or unmodified, film-forming agents, ceramides, preserving agents and opacifiers.

The above adjuvants are generally present in an amount for each of them ranging from 0.01% to 20% by weight, relative to the weight of the dye composition.

Needless to say, a person skilled in the art will take care to select this or these optional additional compounds such that the beneficial properties intrinsically associated with the oxidation dye composition in accordance with the present disclosure are not, or are not substantially, adversely affected by the addition(s) envisaged.

The pH of the dye composition in accordance with the present disclosure generally ranges from about 3 to 12 and according to at least one embodiment, ranges from about 5 to 11. It may be adjusted to the desired value using acidifying or basifying agents usually used in the dyeing of keratin fibers, or alternatively using standard buffer systems.

The acidifying agents that may be mentioned, for example, include but are not limited to inorganic or organic acids such as hydrochloric acid, orthophosphoric acid, sulfuric acid, carboxylic acids such as acetic acid, tartaric acid, citric acid and lactic acid, and sulfonic acids.

Among the basifying agents that may be mentioned, for example, are aqueous ammonia, alkaline carbonates, alkanolamines such as mono-, di- and triethanolamine and derivatives thereof, sodium hydroxide, potassium hydroxide and the compounds of formula (IV) below:

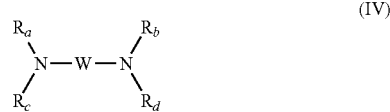

(IV)

wherein:
W is a propylene residue that is unsubstituted or substituted with a hydroxyl group or a $C_1$-$C_4$ alkyl radical; and
$R_a$, $R_b$, $R_c$ and $R_d$, which may be identical or different, are each chosen from a hydrogen atom, a $C_1$-$C_4$ alkyl radical, or a $C_1$-$C_4$ hydroxyalkyl radical.

The dye composition according to the present disclosure may be in various forms, such as in the form of liquids, creams or gels, or in any other form that is suitable for dyeing keratin fibers, such as human hair.

The present disclosure further relates to a process wherein the dye composition according to the present disclosure, as described above, is applied to the fibers, and color is developed using an oxidizing agent. The color may be developed at acidic, neutral or alkaline pH and the at least one oxidizing agent may be added to the composition of the present disclosure just at the time of use, or alternatively, it may be used starting with an oxidizing composition comprising it, which is applied simultaneously or sequentially to the composition of the present disclosure. According to at least one embodiment, this coloration is developed at a neutral pH.

According to at least one embodiment, the composition according to the present disclosure is mixed, for example at the time of use, with a composition comprising, in a medium that is suitable for dyeing, at least one oxidizing agent, wherein this oxidizing agent is present in an amount that is sufficient to develop a coloration. The mixture obtained is then applied to the keratin fibers. After a leave-on time of 3 to 50 minutes, for example 5 to 30 minutes, the keratin fibers are rinsed, washed with shampoo, rinsed again and then dried.

The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which non-limiting mention may be made of peroxidases, 2-electron oxidoreductases such as uricases, and 4-electron oxygenases, for instance laccases. According to at least one embodiment, hydrogen peroxide is used.

The oxidizing composition may also comprise various adjuvants conventionally used in compositions for dyeing the hair and as defined above.

The pH of the oxidizing composition comprising the at least one oxidizing agent is such that, after mixing with the dye composition, the pH of the resulting composition applied to the keratin fibers ranges from 3 to 12, and even further, for example, from 5 to 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels or any other form that is suitable for dyeing keratin fibers, such as human hair.

Another aspect of the present disclosure is a multi-compartment dyeing device or "kit", in which at least one first compartment comprises the dye composition of the present disclosure, as defined above, with the exception of the at least one oxidizing agent, and at least one second compartment comprises at least one oxidizing composition. This multi-compartment kit may be equipped with a means for applying the desired mixture to the hair, such as the devices described in patent FR 2 586 913.

A further aspect of the present disclosure involves the use of the composition of the present disclosure, as described above, for the oxidation dyeing of keratin fibers, for instance human keratin fibers such as the hair.

According to at least one embodiment, the use of the composition in accordance with the present disclosure on natural or permanent-waved grey hair containing 90% white hairs makes it possible to obtain a coloration having, according to the CIELab notation, a value for L* of less than or equal to 50, a value for a* of greater than or equal to 20, for instance greater than or equal to 25, even further, for example from 25 to 50, a value for b* of greater than or equal to 20, for instance greater than or equal to 25, even further, for example, from 25 to 50, and a ratio b*/a* ranging from 0.5 to 1.5, for example from 0.7 to 1.2.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific example is reported as precisely as possible. Any numerical value, however, inherently contains certain errors necessarily resulting from the standard deviation found in its respective testing measurement.

The example that follows serves to illustrate the present disclosure without, however, being limiting in nature.

EXAMPLE

Composition 1 below was prepared:

| | |
|---|---|
| Diethylenetriaminepentaacetic acid, pentasodium salt, as an aqueous 40% solution | 2 g |
| Ammonia as an aqueous 20% solution | 12 g |
| Sodium metabisulfite powder | 0.71 g |
| Pure monoethanolamine | 2.02 g |
| Fumed silica of hydrophobic nature | 1.2 g |
| 2,3-Diamino-6,7-dihydro-1H,5H-pyrazolo[1,2-a]pyrazol-1-one, 2 $CH_3$—$SO_3H$ | 1.9 g |
| 5-Amino-2-methylphenol | 0.2 g |
| Titanium oxide (untreated anatase) coated with polydimethylsiloxane (98/2) | 0.15 g |
| Purified 6-chloro-2-methyl-5-aminophenyl | 0.8 g |
| Para-aminophenol | 0.1 g |
| Glycol distearate | 2 g |
| Mica-titanium oxide-brown iron oxide (58/37.5/4.5) | 0.5 g |
| Fragrance | 0.5 g |
| Tetramethylhexamethylenediamine/1,3-dichloropropylene polycondensate as an aqueous solution | 3 g |
| Non-stabilized polydimethyldiallylammonium chloride at 40% in water | 5 g |
| Carboxyvinyl polymer synthesized in an ethyl acetate/cyclohexane mixture | 0.6 g |
| Deionized water | 24.57 g |
| Propylene glycol | 7 g |
| Natural lauric acid | 3 g |
| Oxyethylenated lauryl alcohol (12 OE) | 7 g |
| Oxyethylenated decyl alcohol (3 OE) | 10 g |
| Cetylstearyl alcohol (50/50 C16-18) (synthetic origin) | 11.5 g |
| Oxyethylenated oleocetyl alcohol (30 OE) | 4 g |
| Vitamin C: L-ascorbic acid as a fine powder | 0.25 |

At the time of use, 1 part by weight of composition 1 was mixed with 1.5 parts by weight of a 25-volumes hydrogen peroxide solution at pH 2.2. A final pH of 9.6 was obtained.

The mixture obtained was applied to locks of natural or permanent-waved grey hair that contained 90% white hairs. After a leave-on time of 20 minutes at room temperature, the locks were rinsed, washed with a standard shampoo, rinsed again and then dried.

The hair coloration was evaluated visually. A coppery light blond shade was obtained.

The color of the hair was measured using a Minolta CM 2002® spectrocolorimeter (illuminant D65-10° CSI) in the CIELab system. In this system, L* represents the lightness, a* the hue and b* the saturation.

The results obtained were given in the table below.

| Type of hair | L* | a* | b* |
|---|---|---|---|
| Natural grey | 44.8 | 31.3 | 34.1 |
| Permanent-waved grey | 38.1 | 35.5 | 29.4 |

What is claimed is:

1. A composition for dyeing keratin fibers, comprising, in a medium suitable for dyeing:

at least one first oxidation base chosen from 2,3-diamino-6,7-dihydro-1H,5H-pyrazolo[1,2-a]pyrazol-1-one, and addition salts thereof;

at least one first coupler chosen from 6-chloro-2-methyl-5-aminophenol, and addition salts thereof; and at least one second coupler chosen from substituted meta-aminophenols of formula (II) below, and addition salts thereof:

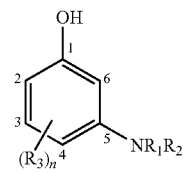

(II)

wherein:

$R_1$ and $R_2$, which may be identical or different, are each chosen from a hydrogen atom; an alkyl radical; a monohydroxyalkyl radical; a polyhydroxyalkyl radical; and a monoaminoalkyl radical; or $R_1$ and $R_2$ form, together with the nitrogen atom to which they are attached, a saturated or unsaturated, 5- to 7-membered cyclic group containing at least one heteroatom, which may be unsubstituted or substituted with at least one radical chosen from carboxyl, carboxamido, hydroxyl, amino, monoalkylamino and dialkylamino radicals, and alkyl radicals optionally substituted with at least one radical chosen from hydroxyl, amino, monoalkylamino and dialkylamino radicals;

$R_3$ is chosen, independently, from a halogen atom, an alkyl radical, an alkoxy radical, a monohydroxyalkyl radical, a polyhydroxyalkyl radical, a monohydroxyalkoxy radical, and a polyhydroxyalkoxy radical;

n is an integer ranging from 0 to 4;

with the provisos that:

when n is equal to 0, then at least one of the radicals $R_1$ and $R_2$ is other than a hydrogen atom;

when n is equal to 2 and $R_3$ is a methyl radical and a chlorine atom, respectively, in positions 2 and 6, and $R_1$ and $R_2$ do not simultaneously represent a hydrogen atom;

it being understood that the at least one first oxidation base and the at least one first coupler are present in a mole ratio of less than 1.5, the at least one first oxidation base and the at least one second coupler are present in a mole ratio of greater than 1, and the molar amount of the at least one first oxidation base is greater than or equal to $2.5 \times 10^{-3}$ mol per 100 g of composition.

2. The composition according to claim 1, wherein $R_1$ and $R_2$, independently of each other, are each chosen from a hydrogen atom, an alkyl radical, and a monohydroxyalkyl radical, or $R_1$ and $R_2$ form, together with the nitrogen atom to which they are attached, a ring chosen from pyrrolidine, piperidine, homopiperidine, piperazine, homopiperazine and morpholine heterocycles; the said rings optionally substituted with at least one radical chosen from hydroxyl, amino, mono($C_1$-$C_2$)alkylamino, di($C_1$-$C_2$)alkylamino, carboxyl and carboxamido radicals, or from $C_1$-$C_4$ alkyl radicals optionally substituted with at least one radical chosen from hydroxyl, amino, mono($C_1$-$C_2$)alkylamino and di($C_1$-$C_2$)alkylamino radicals.

3. The composition according to claim 1, wherein $R_3$ is chosen from a halogen atom, an alkyl radical, an alkoxy radical and a monohydroxyalkoxy radical.

4. The composition according to claim 1, wherein n ranges from 0 to 2.

5. The composition according to claim 1, wherein the substituted meta-aminophenols of formula (II) are chosen from 5-amino-2-methoxyphenol; 5-amino-2-(β-hydroxyethyloxy)phenol; 5-amino-2-methylphenol; 5-N-(β-hydroxyethyl)amino-2-methylphenol; 5-N-(β-hydroxyethyl)amino-4-methoxy-2-methylphenol; 5-amino-4-methoxy-2-methylphenol; 5-amino-4-chloro-2-methylphenol; 6-chloro-2-methyl-5-aminophenol; 5-amino-2,4-dimethoxyphenol; 5-(γ-hydroxypropylamino)-2-methylphenol; 3-dimethylaminophenol; 2-methyl-5-dimethylaminophenol; 2-ethyl-5-dimethylaminophenol; 2-methoxy-5-dimethylaminophenol; 2-ethoxy-5-dimethylaminophenol; 2-(β-hydroxyethyl)-5-dimethylaminophenol; 3-diethylaminophenol; 2-methyl-5-diethylaminophenol; 2-ethyl-5-diethylaminophenol; 2-methoxy-5-diethylaminophenol; 2-ethoxy-5-diethylaminophenol; 2-(β-hydroxyethyl)-5-diethylaminophenol; 3-di(β-hydroxyethyl)aminophenol; 2-methyl-5-di(β-hydroxyethyl)aminophenol; 2-ethyl-5-di(β-hydroxyethyl)aminophenol; 2-methoxy-5-di(β-hydroxyethyl)aminophenol; 2-ethoxy-5-di(β-hydroxyethyl)aminophenol; 2-(β-hydroxyethyl)-5-di(β-hydroxyethyl)aminophenol; 3-pyrrolidin-1-ylphenol; 2-methyl-5-pyrrolidin-1-ylphenol; 2-ethyl-5-pyrrolidin-1-ylphenol; 2-methoxy-5-pyrrolidin-1-ylphenol; 2-ethoxy-5-pyrrolidin-1-ylphenol; 2-(β-hydroxyethyl)-5-pyrrolidin-1-ylphenol; 3-piperidin-1-ylphenol; 2-methyl-5-piperidin-1-ylphenol; 2-ethyl-5-piperidin-1-ylphenol; 2-methoxy-5-piperidin-1-ylphenol; 2-ethoxy-5-piperidin-1-yl phenol; 2-(β-hydroxyethyl)-5-piperidin-1-ylphenol; 3-piperazin-1-ylphenol; 2-methyl-5-piperazin-1-ylphenol; 2-ethyl-5-piperazin-1-ylphenol; 2-methoxy-5-piperazin-1-ylphenol; 2-ethoxy-5-piperazin-1-ylphenol; 2-(β-hydroxyethyl)-5-piperazin-1-ylphenol; 3-(4-methylpiperazin-1-yl)phenol; 2-methyl-5-(4-methylpiperazin-1-yl)phenol; 2-ethyl-5-(4-methylpiperazin-1-yl)phenol; 2-methoxy-5-(4-methylpiperazin-1-yl)phenol; 2-ethoxy-5-(4-methylpiperazin-1-yl)phenol; 2-(β-hydroxyethyl)-5-(4-methyl piperazin-1-yl)phenol; 3-(4-ethylpiperazin-1-yl)phenol; 2-methyl-5-(4-ethylpiperazin-1-yl)phenol; 2-ethyl-5-(4-ethylpiperazin-1-yl)phenol; 2-methoxy-5-(4-ethylpiperazin-1-yl)phenol; 2-ethoxy-5-(4-ethylpiperazin-1-yl)phenol; 2-(β-hydroxyethyl)-5-(4-ethylpiperazin-1-yl)phenol; 3-(4-(β-hydroxyethyl)piperazin-1-yl)phenol; 2-methyl-5-(4-(β-hydroxyethyl)piperazin-1-yl)phenol; 2-ethyl-5-(4-(β-hydroxyethyl)piperazin-1-yl)phenol; 2-methoxy-5-(4-(β-hydroxyethyl)piperazin-1-yl)phenol; 2-ethoxy-5-(4-(β-hydroxyethyl)piperazin-1-yl)phenol; 2-(β-hydroxyethyl)-5-(4-(β-hydroxyethyl)piperazin-1-yl)phenol; 3-morpholin-4-ylphenol; 2-methyl-5-morpholin-4-ylphenol; 2-ethyl-5-morpholin-4-ylphenol; 2-methoxy-5-morpholin-4-ylphenol; 2-ethoxy-5-morpholin-4-ylphenol; and 2-(β-hydroxyethyl)-5-morpholin-4-ylphenol.

6. The composition according to claim 5, wherein the substituted meta-aminophenols of formula (II) are chosen from 5-N-(β-hydroxyethylamino)-2-methylphenol and 5-amino-2-methylphenol.

7. The composition according to claim 1, wherein the at least one first oxidation base/at least one first coupler mole ratio ranges from 0.5 to 1.2.

8. The composition according to claim 1, wherein the at least one first oxidation base/at least one second coupler mole ratio ranges from 2 to 5.

9. The composition according to claim 1, further comprising at least one second oxidation base chosen from para-aminophenols.

10. The composition according to claim 9, wherein the para-aminophenols are chosen from compounds corresponding to formula (III) below, and addition salts thereof:

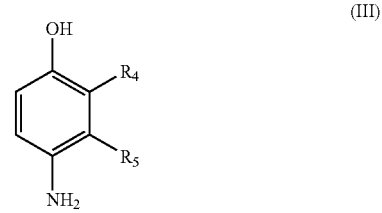

(III)

wherein:

$R_4$ is chosen from a hydrogen atom; a halogen atom; an alkyl radical; a monohydroxyalkyl radical; an alkoxyalkyl radical; an aminoalkyl radical; and a hydroxyalkylaminoalkyl radical;

$R_5$ is chosen from a hydrogen atom; a halogen atom; an alkyl radical; a monohydroxyalkyl radical; a polyhydroxyalkyl radical; an aminoalkyl radical; a cyanoalkyl radical; and an alkoxyalkyl radical;

it being understood that at least one of the radicals $R_4$ or $R_5$ is a hydrogen atom.

11. The composition according to claim 10, wherein the para-aminophenol(s) of formula (III) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol.

12. The composition according to claim 1, further comprising at least one oxidizing agent.

13. A process for dyeing keratin fibers, comprising:

applying a dye composition to the keratin fibers in the presence of at least one oxidizing agent, for a time that is sufficient to develop a desired coloration;

wherein the dye composition comprises, in a medium suitable for dyeing:

at least one first oxidation base chosen from 2,3-diamino-6,7-dihydro-1H,5H-pyrazolo[1,2-a]pyrazol-1-one, and addition salts thereof;

at least one first coupler chosen from 6-chloro-2-methyl-5-aminophenol, and addition salts thereof; and at least one second coupler chosen from substituted meta-aminophenols of formula (II) below, and addition salts thereof:

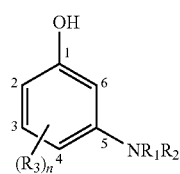

(II)

wherein:
R₁ and R₂, which may be identical or different, are each chosen from a hydrogen atom; an alkyl radical; a monohydroxyalkyl radical; a polyhydroxyalkyl radical; and a monoaminoalkyl radical; or R₁ and R₂ form, together with the nitrogen atom to which they are attached, a saturated or unsaturated, 5- to 7-membered cyclic group containing at least one heteroatom, which may be unsubstituted or substituted with at least one radical chosen from carboxyl, carboxamido, hydroxyl, amino, monoalkylamino and dialkylamino radicals, and alkyl radicals optionally substituted with at least one radical chosen from hydroxyl, amino, monoalkylamino and dialkylamino radicals;

R₃ is chosen, independently, from a halogen atom, an alkyl radical, an alkoxy radical, a monohydroxyalkyl radical, a polyhydroxyalkyl radical, a monohydroxyalkoxy radical, and a polyhydroxyalkoxy radical;

n is an integer ranging from 0 to 4;

with the provisos that:
when n is equal to 0, then at least one of the radicals R₁ and R₂ is other than a hydrogen atom;
when n is equal to 2 and R₃ is a methyl radical and a chlorine atom, respectively, in positions 2 and 6, and R₁ and R₂ do not simultaneously represent a hydrogen atom;

it being understood that the at least one first oxidation base and the at least one first coupler are present in a mole ratio of less than 1.5, the at least one first oxidation base and the at least one second coupler are present in a mole ratio of greater than 1, and the molar amount of the at least one first oxidation base is greater than or equal to $2.5 \times 10^{-3}$ mol per 100 g of composition.

14. A multi-compartment device, comprising:
at least one first compartment comprising a dye composition, wherein the dye composition comprises, in a medium suitable for dyeing:
at least one first oxidation base chosen from 2,3-diamino-6,7-dihydro-1H,5H-pyrazolo[1,2-a]pyrazol-1-one, and addition salts thereof;
at least one first coupler chosen from 6-chloro-2-methyl-5-aminophenol, and addition salts thereof; and
at least one second coupler chosen from substituted meta-aminophenols of formula (II) below, and addition salts thereof:

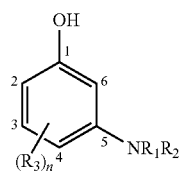

(II)

wherein:
R₁ and R₂, which may be identical or different, are each chosen from a hydrogen atom; an alkyl radical; a monohydroxyalkyl radical; a polyhydroxyalkyl radical; and a monoaminoalkyl radical; or R₁ and R₂ form, together with the nitrogen atom to which they are attached, a saturated or unsaturated, 5- to 7-membered cyclic group containing at least one heteroatom, which may be unsubstituted or substituted with at least one radical chosen from carboxyl, carboxamido, hydroxyl, amino, monoalkylamino and dialkylamino radicals, and alkyl radicals optionally substituted with at least one radical chosen from hydroxyl, amino, monoalkylamino and dialkylamino radicals;

R₃ is chosen, independently, from a halogen atom, an alkyl radical, an alkoxy radical, a monohydroxyalkyl radical, a polyhydroxyalkyl radical, a monohydroxyalkoxy radical, and a polyhydroxyalkoxy radical;

n is an integer ranging from 0 to 4;

with the provisos that:
when n is equal to 0, then at least one of the radicals R₁ and R₂ is other than a hydrogen atom;
when n is equal to 2 and R₃ is a methyl radical and a chlorine atom, respectively, in positions 2 and 6, and R₁ and R₂ do not simultaneously represent a hydrogen atom;

it being understood that the at least one first oxidation base and the at least one first coupler are present in a mole ratio of less than 1.5, the at least one first oxidation base and the at least one second coupler are present in a mole ratio of greater than 1, and the molar amount of the at least one first oxidation base is greater than or equal to $2.5 \times 10^{-3}$ mol per 100 g of composition; and at least one second compartment comprising at least one oxidizing agent.

15. A process for the oxidation dyeing of keratin fibers, comprising:
applying to said keratin fibers a dye composition, where the composition comprises, in a medium suitable for dyeing:
at least one first oxidation base chosen from 2,3-diamino-6,7-dihydro-1H,5H-pyrazolo[1,2-a]pyrazol-1-one, and addition salts thereof;
at least one first coupler chosen from 6-chloro-2-methyl-5-aminophenol, and addition salts thereof; and
at least one second coupler chosen from substituted meta-aminophenols of formula (II) below, and addition salts thereof:

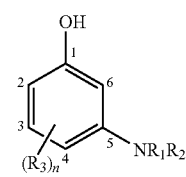

(II)

wherein:
R₁ and R₂, which may be identical or different, are each chosen from a hydrogen atom; an alkyl radical; a monohydroxyalkyl radical; a polyhydroxyalkyl radical; and a monoaminoalkyl radical; or R₁ and R₂ form, together with the nitrogen atom to which they are attached, a saturated or unsaturated, 5- to 7-membered cyclic group containing at least one heteroatom, which may be unsubstituted or substituted with at least one radical chosen from carboxyl, carboxamido, hydroxyl, amino, monoalkylamino and dialkylamino radicals, and alkyl radicals optionally substituted with at least one radical chosen from hydroxyl, amino, monoalkylamino and dialkylamino radicals;

$R_3$ is chosen, independently, from a halogen atom, an alkyl radical, an alkoxy radical, a monohydroxyalkyl radical, a polyhydroxyalkyl radical, a monohydroxyalkoxy radical, and a polyhydroxyalkoxy radical;

n is an integer ranging from 0 to 4;

with the provisos that:
  when n is equal to 0, then at least one of the radicals $R_1$ and $R_2$ is other than a hydrogen atom;
  when n is equal to 2 and $R_3$ is a methyl radical and a chlorine atom, respectively, in positions 2 and 6, and $R_1$ and $R_2$ do not simultaneously represent a hydrogen atom;

it being understood that the at least one first oxidation base and the at least one first coupler are present in a mole ratio of less than 1.5, the at least one first oxidation base and the at least one second coupler are present in a mole ratio of greater than 1, and the molar amount of the at least one first oxidation base is greater than or equal to $2.5 \times 10^{-3}$ mol per 100 g of composition.

16. The process according to claim 15, for obtaining a coloration on natural or permanent-waved grey hair containing 90% white hairs having, according to the CIELab notation, a value for L* of less than or equal to 50, a value for a* of greater than or equal to 20, a value for b* of greater than or equal to 20, and a ratio b*/a* that ranges from 0.5 to 1.5.

* * * * *